(12) United States Patent
Steinmueller (10) Patent No.: US 9,241,627 B2
(45) Date of Patent: Jan. 26, 2016

(54) METHOD AND ANALYSIS SYSTEM FOR EYE EXAMINATIONS

(71) Applicant: Oculus Optikgeraete GmbH, Wetzlar (DE)

(72) Inventor: Andreas Steinmueller, Wettenberg (DE)

(73) Assignee: OCULUS OPTIKGERAETE GMBH, Wetzlar (DE)

( * ) Notice: Subject to any disclaimer, the term of this patent is extended or adjusted under 35 U.S.C. 154(b) by 120 days.

(21) Appl. No.: 14/264,217

(22) Filed: Apr. 29, 2014

(65) Prior Publication Data
US 2014/0320815 A1 Oct. 30, 2014

(30) Foreign Application Priority Data

Apr. 30, 2013 (DE) .................. 10 2013 207 987

(51) Int. Cl.
  *A61B 3/10* (2006.01)
  *A61B 3/00* (2006.01)
  *A61B 3/107* (2006.01)

(52) U.S. Cl.
  CPC .................. *A61B 3/107* (2013.01); *A61B 3/102* (2013.01)

(58) Field of Classification Search
  CPC ..... A61B 3/102; A61B 3/1005; A61B 5/0066
  USPC ............. 351/246, 212, 206, 205, 221
  See application file for complete search history.

(56) References Cited

U.S. PATENT DOCUMENTS 7,425,068 B2   9/2008  Koest
2011/0032480 A1*  2/2011  Rathjen ............. G06K 9/00604
                                                                   351/206

FOREIGN PATENT DOCUMENTS

DE   102005026371 A1   12/2006
EP        2281500 A1    2/2011

OTHER PUBLICATIONS

Ramos, et al., Clinical and Research Applications of Anterior Segment Optical Coherence Tomography—A Review, Clinical and Experimental Ophthalmology, 2009, 37:81-89.

* cited by examiner

*Primary Examiner* — Hung Dang
(74) *Attorney, Agent, or Firm* — Quarles & Brady LLP (57) ABSTRACT

An ophthalmological analysis system for examining an eye, in particular in the region of a front eye section of an eye includes first and second analysis systems obtaining sectional images of the eye. The first analysis system includes a projection device and a monitoring device arranged relative to each other according to the Scheimpflug rule. The second analysis system is an optical coherence interferometer. A processing device processes a first image data set obtained by the first analysis system and a second image data set obtained by the second analysis system to supplement the first image data set, at least partially, with data of the second image data set.

19 Claims, 4 Drawing Sheets

METHOD AND ANALYSIS SYSTEM FOR EYE EXAMINATIONS

CROSS-REFERENCE TO RELATED APPLICATIONS

This application claims priority to German Patent Application No. 10 2013 207 987.7 filed on Apr. 30, 2013, which is fully incorporated herein by reference.

STATEMENT REGARDING FEDERALLY SPONSORED RESEARCH OR DEVELOPMENT

Not applicable.

FIELD OF THE INVENTION

The invention relates to a method and to an ophthalmological analysis system for examining an eye, in particular in the region of a front eye section of an eye, wherein the ophthalmological analysis system comprises a first analysis system for obtaining sectional images of the eye and a second analysis system, wherein the first analysis system is formed from a projection device and from a monitoring device, which are arranged relative to each other according to the Scheimpflug rule, wherein the second analysis system serves for obtaining sectional images of the eye, wherein the second analysis system is formed from an optical coherence interferometer, and wherein the ophthalmological analysis system comprises a processing device.

BACKGROUND OF THE INVENTION

Methods and apparatuses for obtaining sectional images of an eye by means of a Scheimpflug camera are sufficiently known from the state of the art. Thus, for example from document DE 10 2005 026 371, a so-called Scheimpflug recording device is known, with which, by means of a projection device, an eye is illuminated with a light slit, wherein, by means of a monitoring device, a sectional image that is produced in this way is recorded. The monitoring device is substantially formed from a camera, with which an objective lens and image plane intersects an object plane of the sectional image in a joint point. It is further known to store an image data set which has been recorded in this way and, by means of a digital image analysis, to further process said image data set, for example for establishing optical boundary surfaces.

Optical coherence interferometers for an optical coherence tomography (OCT) are likewise sufficiently known from the state of the art. In the field of ophthalmoscopy, said analysis instruments are regularly utilized for examining, in a detailed manner, an eye in the region of a front eye section, of a rear retinal eye section or are also utilized for a so-called full eye scan. In optical coherence interferometry, with the aid of an interferometer, coherent light is utilized for imaging and for distance measurements at reflective and scattering eye tissue. Due to changes in an index of refraction occurring at optical boundary surfaces of the eye and due to volume scatterings, by means of an optical coherence interferometer, measurable signals can be obtained.

The basic principle of optical coherence interferometry is based on white light interferometry and compares the propagation time of a signal with the aid of an interferometer, such as a Michelson interferometer. Here, an optical reference arm of a known optical path length is taken as a reference for an optical measurement arm or measurement beam with which an eye to be examined is scanned. The interference of the signals from the two arms results in a pattern from which a relative optical path length within a depth profile, which is also called A-scan (amplitude-mode scan), can be read. In multidimensional raster methods, a measurement beam can be guided transversely in one or two directions, which results in a planar tomogram, which is also called B-scan (brightness-mode scan). By means of a depth adjustment of a measurement range, a three-dimensional volume can also be recorded as a so-called C-scan (C-mode scan).

Unlike in conventional light microscopy, in optical coherence tonometry, the transverse resolution is decoupled from the longitudinal resolution. The transverse resolution is determined by the numerical aperture of the optics used. The longitudinal spatial resolution into a depth of the material, in contrast, depends on a spectral width of the light used.

With the coherence tonometry methods used in ophthalmology, two basic types can substantially be distinguished. With a first type, a reference arm of an interferometer can be changed with respect to its length and an intensity of the interference can continuously be measured without a spectrum being taken into account here. This method is called time domain method according to a signal measurement in the time domain. With the second type, for determining the measurement values, the spectrum is taken into account and an interference of the individual spectral components is gathered. This method is called frequency domain method. With the frequency domain method, a movable reference is not needed, whereby a simple and quick simultaneous measurement becomes possible. In particular, a complete piece of information on a depth can be established. In frequency domain OCT, two subgroups are again distinguished, with which, on the one hand, the signal is temporally encoded, which means sequentially recorded, or spatially encoded, which means spatially split, but simultaneously recorded. Since the spectral information which has been obtained by means of the spatial splitting of the signal can be gathered by means of a spectrometer, this method is also called spectral domain OCT.

A method for obtaining an OCT full eye scan is further known, with which an optical coherence interferometer can be combined with a further imaging analysis system. Since, using the optical coherence interferometer, tomographic images of different regions of the eye at different reference arm lengths are scanned, these partial scans have to be assembled to a full image of the eye. Here, the partial scans overlap in order to make an accurately fitting combination of obtained image data sets possible. The other analysis system can be employed for supplementing the full eye scan with further image data or, for example, topographic data of the cornea. Here, the full eye scan represents a reference image data set which, according to the requirements of a required eye examination, is partially supplemented with the image data of the other analysis system in the region of the eye section to be examined. This is advantageous since optical boundary surfaces and, in particular, an eye length can be determined in a particularly accurate way using the optical coherence interferometer in contrast to other analysis systems. Thus, a measurement of an eye length having a comparable accuracy is not possible using a Scheimpflug system.

With the known OCT methods, it is disadvantageous that an image record cannot directly be obtained, i.e. that a corresponding period of time is required for scanning the eye section to be recorded by means of the measurement beam. If a depth scan is to be procured, it is moreover required to adapt the reference arm with the corresponding expenditure of time. With the time domain or the frequency domain method, a sequential recording or a spectral tuning of a light source of the coherence interferometer might be required, which likewise prevents a simultaneous recording of an eye section. Thus, eye movements in the time interval of the image recording using the optical coherence interferometer can lead to a falsification of the measurement results. Due to the convex surface of the cornea of the eye, in the case of an offset of the measurement beam perpendicular to the eye in an X axis, there is likewise a distance change in the direction of a Z axis, and there might be an offset in a Y axis. The movement of the eye consequently causes a change in the curvature of the corneal surface relative to the measurement beam and might cause a change in an index of refraction in the examination region of the eye. In particular due to the change in the curvature of the cornea, another measurement error results since the measurement beam is diverted in a deviating way, for example at the corneal surface, due to the movement of the eye and the change in the curvature which is caused thereby. Although movements of the eye can be identified by an offset of a received signal, this does not make a correction of a measurement error possible which results from a change in the curvature.

When recording an image of an eye section using a Scheimpflug system, the problem of measurement errors as a consequence of eye movements occurs only rarely, since the entire sectional image, in contrast to a scanned image, is recorded substantially simultaneously, since an exposure time of a camera chip is comparatively short. If a comparatively quick eye movement is nevertheless effected within an exposure time, a recorded sectional image appears to be blurry. This can, however, during a measurement regularly be prevented due to the simultaneous image recording which is comparatively quick.

SUMMARY OF THE INVENTION

The present invention is therefore based on the task of proposing a method and an apparatus for measuring an eye, using which an image recording with a particularly high resolution of a region of the eye is made possible, wherein measurement errors which are conditioned by a movement of the eye during a measurement time interval are to be avoided.

The method in accordance with the invention for examining or measuring the geometry of a human eye, in particular in the region of a front eye section of an eye, is carried out using an ophthalmological analysis system, wherein the ophthalmological analysis system comprises a first analysis system for obtaining sectional images of the eye, wherein the first analysis system is formed from a projection device and from a monitoring device, which are arranged relative to each other according to the Scheimpflug rule, wherein the ophthalmological analysis system comprises a second analysis system for obtaining sectional images of the eye, wherein the second analysis system is formed from an optical coherence interferometer, wherein the ophthalmological analysis system comprises a processing device, wherein, from at least one coinciding recording plane of the eye, a first image data set is obtained using the first analysis system and a second image data set is obtained using the second analysis system, wherein the processing device processes the first and the second image data set, wherein, by means of the processing device, the first image data set is supplemented, at least partially, with data of the second image data set.

In particular due to the fact that the first image data set, which has been recorded using the first analysis system or a Scheimpflug system, is supplemented or superimposed or combined, at least partially, with the second image data set of the optical coherence interferometer, a substantial improvement of an information density or of an information resolution of the first image data set in a supplemented partial region of the first image data set can be achieved. Since it is only required to procure more detailed image information in a limited region of the first image data set or of the first image record, which region is substantial for a specific eye examination, it is sufficient if the first image data set is only supplemented with the second image data set in the partial region. Then, the second image data set can also be recorded, using the optical coherence interferometer, particularly quickly by scanning a sectional image in the coinciding recording plane of the eye, whereby the risk of a potential movement of the eye when recording the second image data set is considerably reduced. On the whole, it thus becomes possible to gather images of a comparatively large region of an eye, such as a front eye section, using the image recording of a sectional image by the Scheimpflug system or by the first analysis system, and, using the optical coherence interferometer, to represent a selected partial region of the region with a high resolution and in a detailed way, thus avoiding potential measurement errors due to eye movements. The first image data set is supplemented with the data of the second image data set by means of the processing device or means for data processing, by means of which the two image data sets are combined to a resulting image data set. The resulting image data set is geometrically evaluated and the image thereof is illustrated using the known method for image data processing and displaying.

In one embodiment of the method, by means of the second analysis system alone, an image of a cornea of the eye can be recorded using a frequency domain method. An advantage of the frequency domain method is a simple and quick simultaneous measurement, wherein complete information on a depth of the measurement can be established without making a movable reference arm possible. In order to further increase a measurement speed, a spectral domain method can be applied, wherein spectral information of an obtained signal is gathered in parallel, i.e. simultaneously, by means of a spectrometer. A spectral domain OCT system is structured in a comparatively simple way and can be procured at low costs. It is then further possible to take measurements up to a depth of at least 3 mm in the recording plane of the eye.

By means of the second analysis system for obtaining an image record, a depth profile of a cornea of the eye can further be recorded. By means of a so-called amplitude-mode scan or A-scan, a two-dimensional image record or a sectional image from the recording plane of the eye can be obtained. An A-scan can be carried out particularly quickly in contrast to a B-scan or C-scan and is effected by scanning the eye along the recording plane. However, in variant forms of the method, it is also possible to carry out B-scans and C-scans.

It is particularly advantageous if the first and the second image data set are gathered or recorded substantially at the same time. Thus, it can be avoided that an eye movement can be effected between the first image recording and the second image recording. By recording the first and the second image data set simultaneously, potential sources of errors during a measurement are excluded.

Before supplementing the first image data set, the second image data set can further be corrected according to the first image data set. The first image data set can then be taken as a reference image data set after the second image data set has been positioned relative to the first image data set. Potential recording errors in the second image data set, which errors can be caused by an eye movement in the recording period of time of the second image data set, can further be corrected to the effect that, taking account a curvature of a cornea which is known from the first image data set, the second image data set is recalculated at least partially. A change in the curvature of the cornea due to an eye movement during a scan using the optical coherence interferometer can then be taken as a reference for recalculating the partial regions of the eye which have been scanned after the eye movement.

The second image data set can also be oriented or corrected according to optical boundary surfaces which are established from the first image data set, for example by comparing the two image data sets. The optical boundary surfaces which are contained in the first image data set are particularly well-suited for orienting or correcting the second image data set if the same has been falsified by an eye movement. Thus, it is also possible to scale the second image data set according to the first image data set if the second image data set is distorted or has another scale.

By means of the first analysis system, indices of refraction and/or a topography of a cornea can be established, which can be taken into account when correcting the second image data set. Thus, it becomes possible to carry out an even more accurate correction of the second image data set.

Preferably, the first image data set can be superimposed with the second image data set. Thus, it becomes possible to superimpose less detailed representations of a partial region of the first image data set with more detailed representations of the second image data set in such a way that the region in question of the first image data set is covered or, alternatively, recalculated by additive image processing.

In order to procure a three-dimensional image data set of an eye, a plurality of first and second image data sets can be obtained in a sequential order, wherein the joint recording plane of the first and of the second analysis system can be pivoted about a visual axis of the eye. The sectional images which are recorded in the sequential order are then assembled, by means of the processing device, to a three-dimensional model of the eye. The first and the second analysis system can at least rotate by 180° about the visual axis in order to thus pivot the recording plane uniformly above the region of the front eye section. Hence, the recording plane can axially be rotated about the visual axis, wherein up to 100 sectional images can be recorded one after the other at different angles α relative to a horizontal plane using the first and the second analysis system, respectively.

It is also advantageous if a relative position of at least one optical boundary surface of the eye, which surface is established using the first analysis system, is determined as a reference surface or as a reference point for the second analysis system. By means of the first analysis system, a relative position of the eye to be examined relative to the analysis system can particularly accurately be determined. Thus, eye movements can also simply be identified when recording a sequence of sectional images. A sectional image which is obtained using the second analysis system can then particularly simply be correctly arranged in terms of space, with respect to the eye, according to the associated sectional image of the first analysis system or to the associated sectional image record of the sequence of the first analysis system. An optical boundary surface of the eye, such as the corneal surface, can be taken as a reference surface or line or point.

The first analysis system and the second analysis system can respectively emit light or electromagnetic radiation of different wavelength ranges. Due to this fact, it is possible to achieve the advantage that the respective beam paths can be identical, wherein, via suitable optical filters, the beam paths can be separated or images can be gathered separately from one another. For example, for the optical coherence interferometer, light of a wavelength of 800 nm can advantageously be used since it is then possible to utilize infrared sensors which can be procured at low costs in regular stores. The projection device of the first analysis system can, for example, emit light of a wavelength of 475 nm. Apart from that, it is thus also avoided to the greatest possible extent that a person which is to be examined is blinded.

The ophthalmological analysis system in accordance with the invention for examining or measuring a geometry of an eye, in particular in the region of a front eye section of an eye, comprises a first analysis system for obtaining sectional images of the eye, wherein the first analysis system is formed from a projection device and from a monitoring device, which are arranged relative to each other according to the Scheimpflug rule, and further comprises a second analysis system for obtaining sectional images of the eye, wherein the second analysis system is formed from an optical coherence interferometer, wherein the ophthalmological analysis system comprises a processing device, wherein, from at least one coinciding recording plane of the eye, a first image data set can be obtained using the first analysis system and a second image data set can be obtained using the second analysis system, wherein the processing device is constructed such that said device is able to process the first and the second image data set, wherein, by means of the processing device, the first image data set can, at least partially, be supplemented with data of the second image data set. Concerning the advantages of the ophthalmological analysis system in accordance with the invention, reference is made to the description of the advantages of the method in accordance with the invention.

The second analysis system can comprise, other than the optical coherence interferometer, a beam guidance device, such as a mirror, a prism or a lens, by means of which a measurement beam of the optical coherence interferometer can be projected onto the cornea, wherein the measurement beam can be diverted within or in the recording plane such that the eye can be scanned by the measurement beam along the recording plane for obtaining a second image data set. Consequently, the beam guidance device can divert or deflect a beam path of the second analysis system as a measurement beam, such that the measurement beam is situated in the recording plane. For recording a sectional image, the measurement beam can then be moved through the recording plane or along a line in which the recording plane intersects a cornea of an eye. For example, for obtaining a sectional image, by means of the optical coherence interferometer, at least 4000 measurement points per sectional image can be measured, having a lateral resolution of approximately 4 µm.

The beam guidance device can further be constructed such that the measurement beam can be projected onto a surface point of a cornea, wherein the measurement beam can be projected onto the cornea relative to a tangent plane of the surface point, at an angle which deviates from 90°. The surface point hence corresponds to the point in which the measurement beam strikes the cornea. Since the measurement beam then strikes the cornea relative to the tangent plane rather than vertically, the measurement beam is not directly reflected from the surface of the cornea. A direct reflection is very bright and can lead to irradiations when detecting the reflected beam, which irradiations are hard to correct. Such irradiations can thus effectively be avoided.

The beam guidance device can alone have a movable tilting mirror which is arranged between the eye to be examined and the second analysis system, wherein the tilting mirror can then be arranged in a measurement axis of the analysis system. Using the tilting mirror, it is then possible to deflect a beam path of the second analysis system as a measurement beam, which path runs relative to the eye. Preferably, the second analysis system can be constructed such that the beam path runs in the direction of a visual axis of the eye and strikes the tilting mirror which then diverts the measurement beam. Since gathering a sectional image only requires a linear scan of the eye by means of the measurement beam, a tilting mirror is alone needed. Gathering a sectional image or a second image data set can, for example, be effected within 20 to 40 milliseconds. Then, it is also possible to record the second image data set substantially simultaneously with the first image data set.

The ophthalmological analysis system can particularly easily be constructed if beam paths of the first and of the second analysis system jointly run on the measurement axis, and if the tilting mirror then is a dichroic mirror. Using the dichroic mirror, it is then possible to separate the respective beam paths. For example, the dichroic mirror can be constructed such that only light of the second analysis system is reflected. Light of the first analysis system can then pass through the tilting mirror without being reflected.

The beam guidance device can further have an aspherical concave mirror, which can be arranged to follow a tilting mirror in the direction of a beam path of the second analysis system and by means of which the beam path or a measurement beam of the second analysis system can be deflected onto a cornea of an eye to be examined, wherein the concave mirror can be constructed such that an optical path length of the beam path of the second analysis system or of a measurement arm of the optical coherence interferometer up to the cornea can substantially remain unchanged when scanning different points of the cornea. Hence, the measurement beam that is diverted from the tilting mirror can be deflected onto the aspherical concave mirror and can then be diverted from the aspherical concave mirror onto the cornea of the eye. By the concave or aspherical concave mirror, it then becomes possible to keep the length of the measurement arm or of the associated beam path of the optical coherence interferometer substantially constant or identical relative to a surface of the cornea. An axial measurement range or a measurement depth of the optical coherence interferometer can thus substantially be adapted to the surface of the cornea.

Thus, a measurement range of the second analysis system can be adapted to a curvature of a cornea. Here, it is initially irrelevant how the curvature adaptation is effected. Depending on the shape of the concave mirror, the measurement range can have a depth of at least 3 mm in the recording plane and can be constructed in the shape of an arch, being adapted to the sectional shape of the cornea. In such a design of the ophthalmological analysis system, a measurement distance to an eye to be examined can, for example, amount to approximately 80 mm.

In order to procure image data sets that make a three-dimensional reproduction of an eye possible, the joint recording plane of the first and of the second analysis system can be pivotable about a visual axis of the eye by means of a rotation device, wherein the optical coherence interferometer can then have an optical fiber or a fiber optical waveguide which is mechanically decoupled from the rotation device. The rotation device can, for example, be constructed by the first analysis system, wherein a camera in a Scheimpflug arrangement can be rotated, together with the projection device or a slit illumination, about the visual axis or a measurement axis of the eye. Simultaneously, a measurement beam of the optical coherence interferometer can be rotated relative to the recording plane by means of a beam guidance device. If a beam path of the optical coherence interferometer of the rotating beam guidance device is fed via a fiber optical waveguide, it might be required to mechanically decouple the optical fiber waveguide from the turn of the beam guidance device or of the rotation device. This is in particular required if a completely free turn of the rotation device is possible. A spectrometer of the optical coherence interferometer can further also be integrated into an instrument housing of the first analysis system. Moreover, it is possible to construct the first and the second analysis system in a joint housing.

Further advantageous embodiments of the ophthalmological analysis system result from the descriptions of the features of the dependent claims which relate back to the method in accordance with the invention.

BRIEF DESCRIPTION OF THE DRAWINGS

In the following, preferred embodiments of the method and of the ophthalmological analysis system are explained in more detail with the aid of the drawings.

In the figures.

DETAILED DESCRIPTION OF THE EXAMPLE EMBODIMENTS

Figure 4:
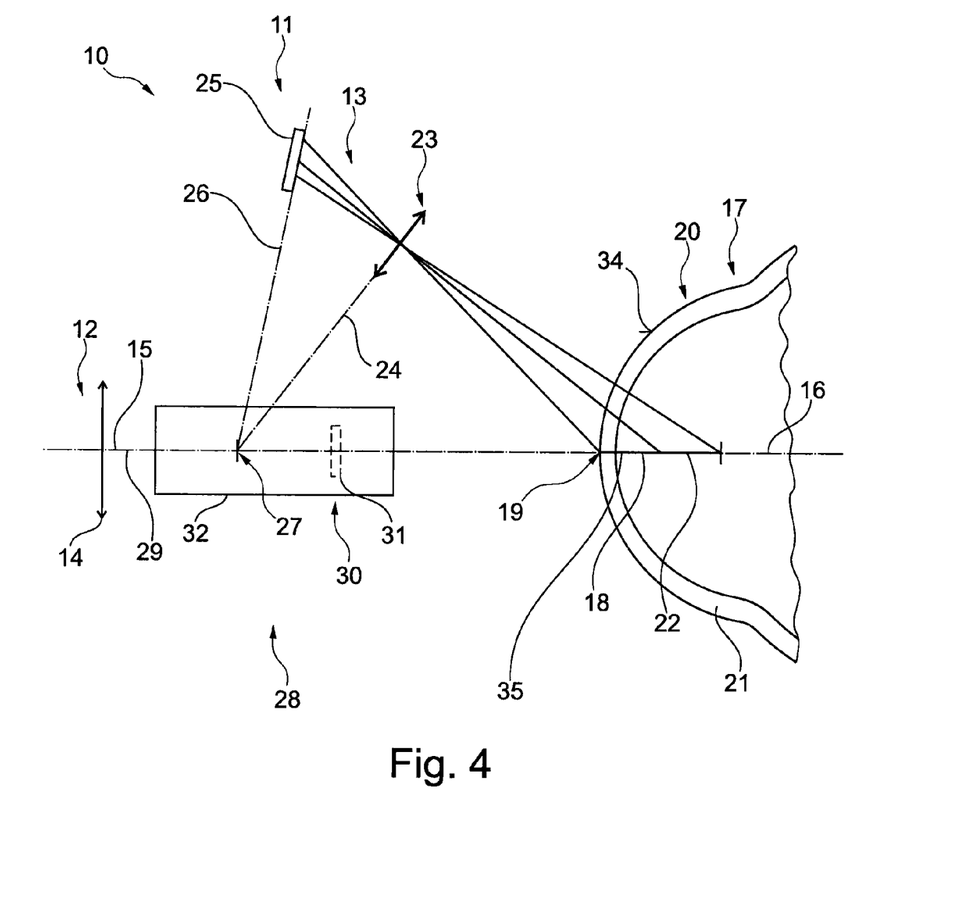
FIG. 4 shows a partial schematic illustration of an instrument structure together with a partial sectional view of the eye in a side view.
Figure 5:
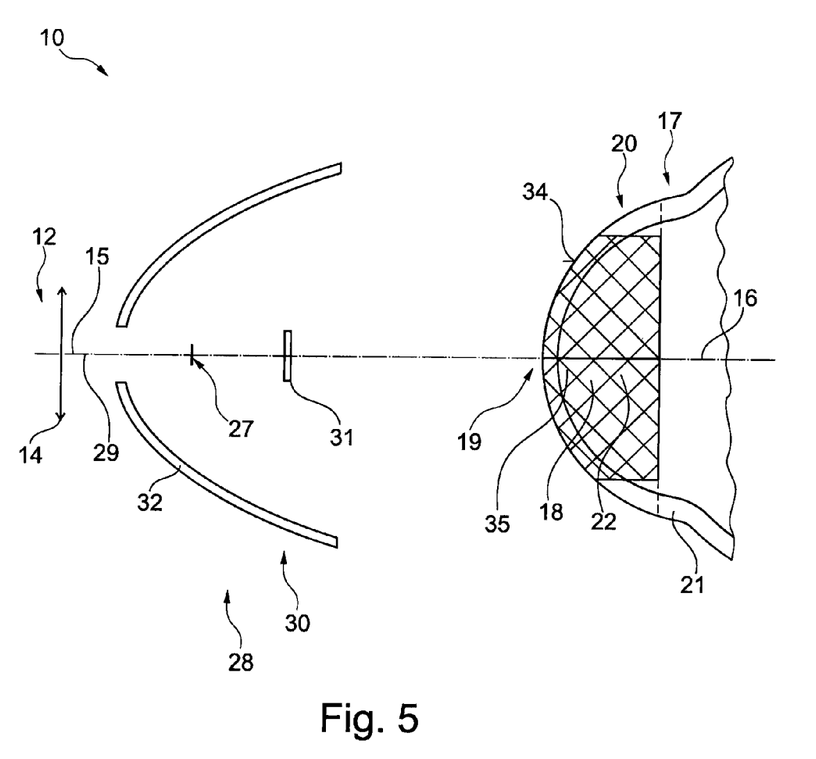
FIG. 5 shows the partial schematic illustration from FIG. 4 in a top view.

The basic structure of an ophthalmological analysis system 10 can be taken from FIGS. 4 and 5. A first analysis system 11, which is partially illustrated here, of the ophthalmological analysis system 10 is formed from a projection device 12 and from a monitoring device 13. As regards the projection device 12, only an objective lens 14 is schematically indicated here, through which objective lens a beam path 15 of a slit illumination, which is not illustrated in more detail here, is projected onto the eye 17 along a visual axis 16 of an eye 17. In FIGS. 4 and 5, the beam path 15 of the slit illumination runs in a recording plane 18, such that the slit illumination or the recording plane 18 runs horizontally and orthogonally relative to a viewing plane of FIG. 4 or parallel to a viewing plane of FIG. 5. The beam path 15, in the region of an apex 19 of the eye 17, enters a front eye section 20 having a cornea 21 of the eye 17, which cornea is schematically illustrated here, and produces a sectional image 22 within the eye 17 due to light scattering, which sectional image is illustrated with criss-cross lines in FIG. 5. The sectional image 22 is recorded by means of the monitoring device 13, which is formed from an objective lens 23 having a principal plane 24 and a camera chip 25. An image plane 26 of the camera chip 25 as well as the principal plane 24 are oriented such that they intersect the recording plane 18 in a point 27, such that the Scheimpflug rule is fulfilled for the monitoring device 13. Consequently, the sectional image 22 is depicted in a distortion-free way on the camera chip 25. A second analysis system 28 of the ophthalmological analysis system 10 is formed from an optical coherence interferometer, which is not illustrated in more detail here, and which employs the objective lens 14 of the monitoring device 13. A beam path 29 of the second analysis system 28 is identical with the beam path 15 of the projection device 12 or of the visual axis 16 and represents a measurement arm of the optical coherence interferometer. The second analysis system further comprises a beam guidance device 30 having a dichroic tilting mirror 31 and an aspherical concave mirror 32. The aspherical concave mirror 32 is constructed in two pieces.

Figure 1:
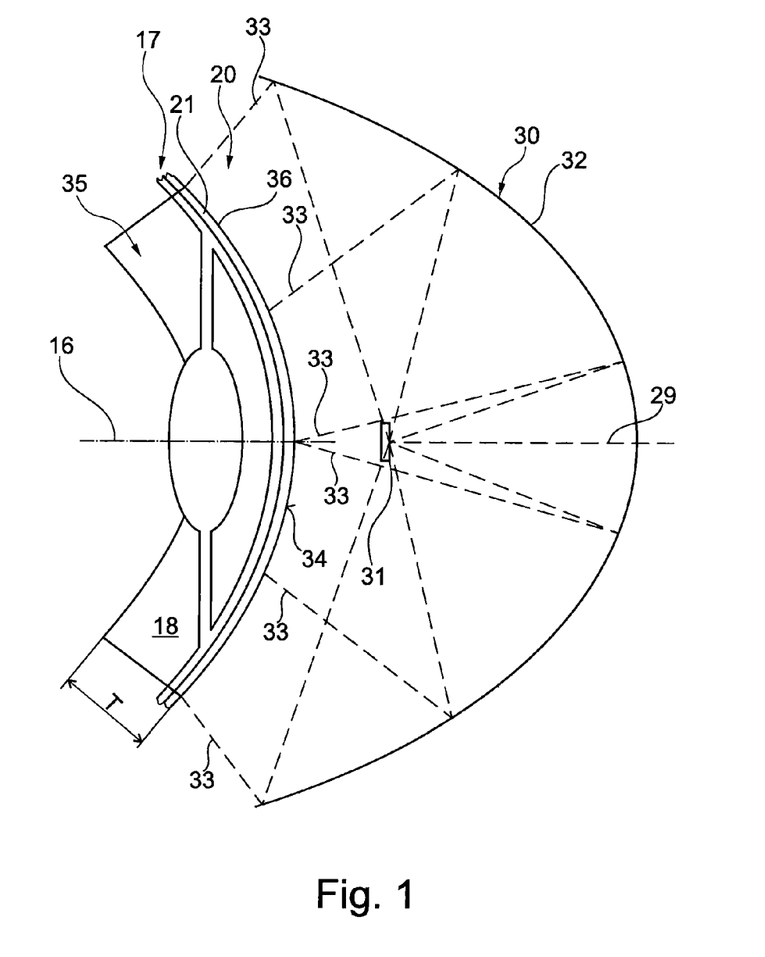
FIG. 1 shows a schematic view of a front eye section together with an embodiment of a beam guidance device.

The schematic view which is shown in FIG. 1 corresponds to a top view onto the recording plane 18 which runs horizontally in FIG. 4.

As can be seen from a combined view of FIGS. 1 and 4, the beam path 29 of the second analysis system 28, after passing through the objective lens 14, is reflected within the recording plane 18 by the tilting mirror 31 and is projected onto the aspherical concave mirror. The aspherical concave mirror 32 reflects the beam path 29 onto the cornea 21 of the eye 17. After FIG. 1, the beam path 29 can be diverted in a plurality of directions within the recording plane 18 as one measurement beam 33 above the tilting mirror 39, as can be seen from FIG. 1, and can penetrate the eye 17 up to a measurement depth T of at least 3 mm. Here, using the optical coherence interferometer, a spectral domain scan is carried out, during which an axial resolution or depth resolution of 1 to 5 µm is achieved, and wherein at least 4000 measurement points are recorded along the cornea 21 in the recording plane 18.

It is further envisaged that the beam path 15 and the beam path 29 are respectively made up of light of different wavelengths, such that only the beam path 29 is reflected by the dichroic tilting mirror 31 and the beam path 15 can penetrate the dichroic tilting mirror 31 in an unimpeded way.

By the cooperation of the tilting mirror 31 and of the aspherical concave mirror 32, a length of the beam path 29 or of the measurement beam 33 is relatively adapted with respect to a surface 34 of the cornea 21, such that a sectional image 35 of the second analysis system 28 is adapted to a contour 36 of the surface 34 of the cornea 21 and substantially runs in the shape of an arch. Therefore, an optical coherence interferometer can be used with a rigid and non-displaceable reference arm and a measurement range of the second analysis system can be adapted, in an optimum way, to the eye 17 to be measured.

Figure 3:
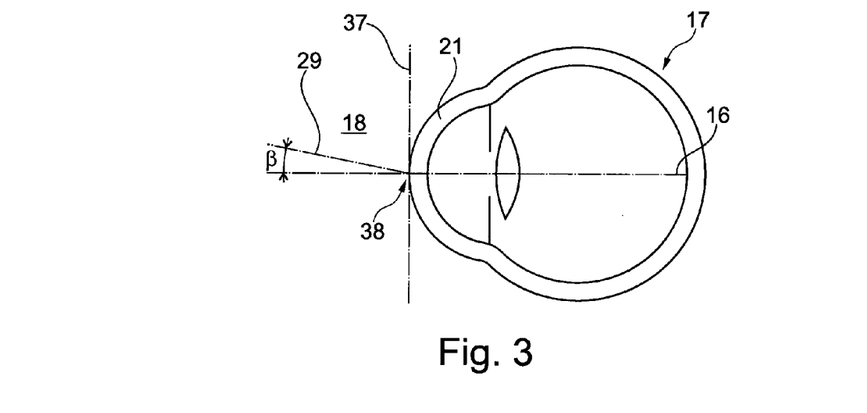
FIG. 3 shows a sectional view of the eye in a recording plane.

In order to avoid a direct reflection of the measurement beam 33, and, in connection therewith, crossfades at a detector of a spectrometer of the optical coherence interferometer, the measurement beam 33, as can be seen from the schematic illustration in FIG. 3, is projected onto the cornea 21 relative to a tangent plane 37 of a surface point 38 of the cornea 21, which point is met by the measurement beam 33, at an angle β which deviates from 90°. FIG. 3 here shows a top view onto the recording plane 18.

Figure 2:
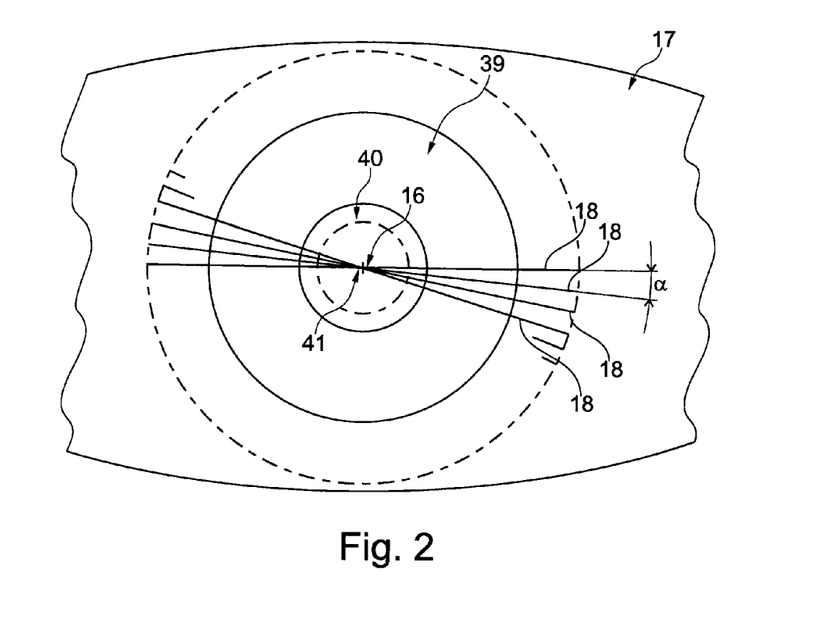
FIG. 2 shows a front view of an eye in the direction of a visual axis.

FIG. 2 shows a schematic front view of the eye 17, having an iris 39 and a pupil 40 as well as a rotation axis 41 on the visual axis 16. The projection device 12 or the slit illumination having the monitoring device 13 can now be turned about the rotation axis 41 together with the tilting mirror 31, such that the recording plane 18 can be pivoted about the visual axis 16 or the rotation axis 41 by an angle α. By a rotation or turn by at least 180° and by recording sectional images 22 and 35, respectively, using the first analysis system 11 and the second analysis system 28 in each position of the recording plane 18, it is then possible to procure a plurality of sectional images 22 and 35 of the eye 17, in order to combine said images, by means of a processing device of the ophthalmological analysis system, which device is not shown here, to form a three-dimensional image of the eye 17 or of the front eye section 20 thereof. Here, in particular for the sectional images 22 and 35, respectively, of each recording plane 18, a first image data set of the first analysis system 11, respectively, is supplemented, at least partially, with data of a second image data set of the second analysis system 28. Thus, it is then possible to supplement the sectional image 22, which has a comparatively larger surface compared to the sectional image 35, with image data of the sectional image 35 and to achieve, in the region of the sectional image 35, a more detailed illustration of the eye 17 within a partial region of the sectional image 22.

The invention claimed is:

1. A method for examining an eye, in particular in the region of a front eye section of an eye, said method comprising:
   obtaining a first image data set of sectional images of the eye from at least one coinciding recording plane using a first analysis system, said first analysis system including a projection device arranged relative to a monitoring device according to the Scheimpflug rule;
   obtaining a second image data set of sectional images of the eye from the at least one coinciding recording plane using a second analysis system, said second analysis system including an optical coherence interferometer; and
   processing the first and the second image data sets, using a processing device, wherein processing the first and second image data sets includes supplementing the first image data set, at least partially, with data of the second image data set.

2. The method according to claim 1, in which the second analysis system records an image of a cornea of the eye using a frequency domain method.

3. The method according to claim 1, in which the second analysis system obtains an image record by recording a depth profile of a cornea of the eye.

4. The method according to claim 1, in which the first and the second image data set are obtained at the same time.

5. The method according to claim 1, in which before supplementing the first image data set, the second image data set is corrected according to the first image data set.

6. The method according to claim 5, in which the second image data set is corrected according to optical boundary surfaces which are established from the first image data set.

7. The method according to claim 5, in which the first analysis system establishes indices of refraction and/or a topography of a cornea, which are taken into account in the correction.

8. The method according to claim 1, in which the first image data set is superimposed with the second image data set.

9. The method according to claim 1, in which a plurality of first and second image data sets is obtained in a sequential order, wherein the at least one coinciding recording plane of the first and of the second analysis system is pivoted about a visual axis of the eye.

10. The method according to claim 1, in which a relative position of at least one optical boundary surface of the eye, which surface is established using the first analysis system, is determined as a reference surface for the second analysis system.

11. The method according to claim 1, in which the first analysis system and the second analysis system respectively emit light of different wavelength ranges.

12. An ophthalmological analysis system for examining an eye, in particular in the region of a front eye section of an eye, said analysis system comprising:
   a first analysis system for obtaining a first image data set of sectional images of an eye from at least one coinciding recording plane, wherein the first analysis system includes a projection device and a monitoring device, said projection device and said monitoring device being arranged relative to each other according to the Scheimpflug rule;

a second analysis system for obtaining a second image data set of sectional images of the eye from the at least one coinciding recording plane, wherein the second analysis system includes an optical coherence interferometer; and a processing device processing the first image data set and the second image data set, to supplement the first image data set can, at least partially, with data of the second image data set.

13. The analysis system according to claim 12, in which the second analysis system includes a beam guidance device projecting a measurement beam of the optical coherence interferometer onto the cornea, wherein the measurement beam can be diverted within the recording plane such that the eye can be scanned by the measurement beam along the recording plane.

14. The analysis system according to claim 13, in which the beam guidance device is constructed such that the measurement beam can be projected onto a surface point of a cornea, wherein the measurement beam can be projected onto the cornea relative to a tangent plane of the surface point at an angle which deviates from 90°.

15. The analysis system according to claim 13, in which the beam guidance device has a movable tilting mirror which is arranged in a measurement axis of the analysis system.

16. The analysis system according to claim 15, in which beam paths of the first and of the second analysis system jointly run on the measurement axis, and wherein the tilting mirror is a dichroic mirror.

17. The analysis system according to any one of claim 13, in which the beam guidance device has a concave mirror, by means of which a beam path or a measurement beam of the second analysis system can be deflected onto a cornea, wherein the concave mirror is constructed such that an optical path length of the beam path up to the cornea substantially remains unchanged when scanning different points of the cornea.

18. The analysis system according to claim 12, in which a measurement range of the second analysis system is adapted to a curvature of a cornea.

19. The analysis system according to claim 12, in which the coinciding recording plane of the first and of the second analysis system can be pivoted about a visual axis of the eye by means of a rotation device, wherein the optical coherence interferometer has an optical fiber which is mechanically decoupled from the rotation device.

* * * * *